US010328375B2

(12) United States Patent
Bazer-Bachi et al.

(10) Patent No.: US 10,328,375 B2
(45) Date of Patent: Jun. 25, 2019

(54) COLLECTOR ASSEMBLY FOR A GASEOUS FLUID FOR A RADIAL REACTOR (71) Applicant: IFP Energies nouvelles, Rueil-Malmaison (FR)

(72) Inventors: Frederic Bazer-Bachi, Irigny (FR); Cecile Plais, Les Haies (FR); Eric Sanchez, Saint Genis Laval (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 426 days.

(21) Appl. No.: 15/061,616

(22) Filed: Mar. 4, 2016

(65) Prior Publication Data
US 2016/0256812 A1    Sep. 8, 2016

(30) Foreign Application Priority Data

Mar. 5, 2015    (FR) .................................... 15 51832

(51) Int. Cl.
*B01J 4/00*        (2006.01)
*B01J 8/12*        (2006.01)
*B01D 46/24*       (2006.01)
*C07C 6/04*        (2006.01)
*B01J 8/02*        (2006.01)
(Continued)

(52) U.S. Cl.
CPC ..... *B01D 46/2403* (2013.01); *B01D 46/0024* (2013.01); *B01J 4/005* (2013.01);
(Continued)

(58) Field of Classification Search
CPC ... B01J 8/12; B01J 2208/00884; C10G 11/16; C10G 25/08; C10G 35/12; C10G 45/18; C10G 47/28; C10G 49/14
(Continued)

(56) References Cited

U.S. PATENT DOCUMENTS 3,027,244 A * 3/1962 Byrne .................... B01J 8/0214
                                                     208/146
3,909,208 A    9/1975 Boret et al.
(Continued)

FOREIGN PATENT DOCUMENTS

EP    0483975 A1    5/1992
FR    2953738 A1    6/2011

OTHER PUBLICATIONS

Search Report for FR1551832 dated Jan. 7, 2016.
English Abstract of FR2953738, Publication Date: Jun. 17, 2011.

*Primary Examiner* — Jennifer A Leung
(74) *Attorney, Agent, or Firm* — Millen White Zelano & Branigan, PC (57) ABSTRACT The invention concerns a collector assembly (8) for a gaseous fluid suitable for being disposed in a reaction section with a moving bed of catalyst of a radial reactor. The collector assembly comprises a vertical cylindrical screen (9), permeable to gas and impermeable to particles of catalyst, and a vertical cylindrical tube (10) which is supported by this screen (9) and disposed in a concentric manner with respect to the screen. The tube (10) comprises one or more zones (17*a*, 17*b*) which are permeable to gaseous fluid, comprising a plurality of through holes and a plurality of zones (18*a*, 18*b*, 18*c*, 18*d*) with a reduced permeability to gaseous fluid compared with the permeable zone. Each zone with a reduced permeability has a porosity, defined as the ratio between total permeable surface area of the zone and total developed surface area of this zone, in the range 0 to 0.005.

29 Claims, 4 Drawing Sheets (51) Int. Cl.
*C07C 5/27* (2006.01)
*B01D 46/00* (2006.01)

(52) U.S. Cl.
CPC .......... *B01J 8/0214* (2013.01); *B01J 8/0278* (2013.01); *B01J 8/12* (2013.01); *C07C 5/27* (2013.01); *C07C 6/04* (2013.01); *B01J 2208/00752* (2013.01); *B01J 2208/00761* (2013.01); *B01J 2208/00884* (2013.01); *B01J 2208/00893* (2013.01); *B01J 2208/00938* (2013.01)

(58) Field of Classification Search
USPC ........................................................ 208/165
See application file for complete search history.

(56) References Cited

U.S. PATENT DOCUMENTS

| | | | |
|---|---|---|---|
| 4,110,081 A * | 8/1978 | Millar | B01J 8/003 208/165 |
| 4,277,444 A | 7/1981 | Van Landeghen et al. | |
| 4,374,095 A * | 2/1983 | Legg | B01J 8/0214 208/146 |
| 5,250,270 A * | 10/1993 | Noe | B01J 8/0214 422/148 |
| 6,221,320 B1 | 4/2001 | Nagaoka et al. | |
| 2013/0343961 A1* | 12/2013 | Vetter | B01J 8/0257 422/218 |

\* cited by examiner

COLLECTOR ASSEMBLY FOR A GASEOUS FLUID FOR A RADIAL REACTOR

The present invention relates to a collector assembly for a gaseous fluid for moving bed units having a radial movement of the feed, which involves a flow through a catalytic bed in a set of directions corresponding to radii orientated from the periphery towards the centre or from the centre of the vessel towards the periphery. The present invention also relates to a radial bed reactor comprising a collector assembly for gaseous reaction effluent. Finally, the invention relates to a process for the catalytic conversion of a hydrocarbon feed employing a radial bed reactor.

PRIOR ART

The most representative unit for this type of radial flow is one for regenerative reforming of gasoline type hydrocarbon cuts which may be defined as having a distillation interval in the range 80° C. to 250° C. However, the field of application of the present invention is broader, and in addition to the catalytic reforming of gasolines, the skeletal isomerization of various C4, C5 olefinic cuts or indeed the metathesis process for the production of propylene may also be mentioned, for example. This list of processes is not exhaustive, and the present invention may be applied to any type of catalytic process with a radial flow and a gaseous feed. Thus, in the context of new energy technologies, alcohol to alkene processes, for example, could employ this type of technology.

Certain of these radial bed units, including regenerative reforming, use a flow of catalyst known as a moving bed, i.e. a slow gravitational flow of particles of catalyst (or catalytic bed) confined in an annular space delimited by the wall of the reactor and an inner wall which is permeable to gas and impermeable to grains of catalyst which corresponds to the collection conduit (or central collector) which recovers the reaction effluents.

Alternatively, the moving catalytic bed may be confined in a space, which is generally annular, formed between a screen called the "outer" screen and the collection conduit which are preferably disposed in a concentric manner. The "outer" screen may be constituted by an assembly of screen elements in the form of scallops. The gaseous feed is generally introduced via the outer periphery of the annular bed and passes through the catalytic bed in a manner which is substantially perpendicular to the vertical direction of flow of the latter. The reaction effluents are then recovered in the collection conduit (or collector).

However, the use of this type of reactor is limited in terms of feed flow rate. In fact, too high a feed flow rate will lead to the phenomenon of the catalyst becoming stuck against the central collector (known as "pinning"). The force exerted by the feed moving radially from the outer periphery of the catalyst bed towards the centre over the grains of catalyst pins them against the wall of the central collector, which increases the frictional load which then opposes sliding of the grains along the wall. If the flow of feed is sufficiently high, then the frictional force which results is sufficient to support the weight of the catalytic bed and thus the gravitational flow of the grains of catalyst ceases, at least in certain regions adjacent to the wall of the central collector. In these regions, the grains of catalyst are then pinned by the flow of gas and are immobilized against the wall of the collector. The phenomenon of immobilization of the grains of catalyst is to be avoided as much as possible in catalytic reactors, for example those for the catalytic reforming of a hydrocarbon feed, because it favours catalyst deactivation reactions (for example coking), ultimately preventing the reactor from continuing to operate properly. Potentially, when the cake of catalyst becomes too thick along the conduit, it is then necessary to reduce the flow rate of the gas to be treated or even to stop the unit in order to clean out said conduit.

Furthermore, when the pressure drop is not constant over the total height of the central collector, this generates preferential pathways (known as "channelling") in the reaction section which are then used by the gaseous fluid. Depending on the direction of flow of the gaseous fluids, these preferential pathways may be located in the upper or lower portions of the reaction section, and generate disparities in the contact time between the gaseous fluid and the catalyst in the reaction section, which may be at the origin of reductions in the conversion yield and/or in the selectivity of the catalytic reaction.

Thus, in the question of homogeneous distribution of the feed, it is desirable to balance the total pressure drop between the catalytic bed and the collector tube over the entire height of the catalytic bed as far as possible. One method employed consists of adding a tube which has been perforated in a uniform manner over the central collector, which produces a much higher pressure drop than that experienced by the gaseous fluid along its path in the catalytic bed.

One aim of the invention is to provide a device for collecting a gaseous fluid for a radial reactor which, when employed in said reactor, is less subject to the phenomenon of pinning and for which the pressure drop is capable of being controlled in a manner such as to limit the disparities and thus reduce the risks of the formation of preferential pathways for the gaseous fluid in the catalytic bed.

SUMMARY OF THE INVENTION

Thus, the present invention concerns a collector assembly for a gaseous fluid which can be disposed in a reaction section with a moving bed of catalyst of a radial reactor, said collector assembly comprising a vertical cylindrical screen which is permeable to gaseous fluid and impermeable to particles of catalyst, and a vertical cylindrical tube which is supported by said screen and disposed in a concentric manner with respect to said screen. The tube, which is permeable to gaseous fluid and impermeable to particles of catalyst, comprises one or more zones which are permeable to gaseous fluid comprising a plurality of through holes and a plurality of zones with a reduced permeability to gaseous fluid compared with the zone which is permeable to gaseous fluid. Each zone with reduced permeability has a lower porosity than that of a zone which is said to be permeable. The porosity of a zone is defined by the ratio between the total permeable surface area of said zone and the total developed surface area of said zone. In accordance with the invention, the porosity of a zone with reduced permeability is in the range 0 to 0.005, it being understood that a "zone with reduced permeability" excludes any space comprised between the through holes of the permeable zone or zones.

The Applicant has established that using a perforated tube with one or more zones with reduced permeability close-coupled with the screen in order to form a collector assembly means that the pressure drop at said screen can be controlled. By adjusting the porosity of the cylindrical tube, it is then possible to generate different pressure drops over the height of the collector screen and thus to adapt the pressure drops as a function of this height.

Surprisingly, the Applicant has established that the presence of zones with a reduced permeability to the gaseous fluid formed on the tube also means that pinning of the catalyst against the screen can be reduced compared with a simple screen without a close-coupled tube. The collector assembly of the invention can thus be used to solve two problems, without the need for modification to the screen, which is a complex part which is fragile by design.

In the context of the invention, the collector assembly is suitable for use in moving bed catalytic reactors and with radial movement of the gaseous feed, i.e. into which the catalyst is introduced into the reaction zone continuously or discontinuously and withdrawn from the reactor continuously or discontinuously.

In accordance with the invention, the total developed surface area of the zones with "reduced permeability" is generally in the range 1% to 30% of the total developed surface area of the tube.

In accordance with a particular embodiment, the section of the screen and the tube is polygonal in shape with at least 3 sides, it being understood that the number of sides of the sections of the screen and tube are equal.

In accordance with a particular embodiment, the porosity of the zone with reduced permeability is equal to 0 in a manner such as to form a solid zone, it being understood that a solid zone excludes any solid space comprised between the through holes of a permeable zone.

In accordance with another embodiment, the porosity of the zone with reduced permeability is other than 0 and said zone comprises through holes.

Preferably, the through holes of a zone with reduced permeability are spaced from each other by a pitch which is higher than the pitch between the through holes of a zone which is permeable to gaseous fluid.

In accordance with another embodiment, the surface area of the through holes of the zone with reduced permeability is smaller than the surface area of the through holes of a zone which is permeable to gaseous fluid.

The zones with reduced permeability may be extended, forming an angle $\alpha$ in the range 0° to 90° with respect to the horizontal.

In a preferred embodiment, the screen of the collector assembly is formed by a plurality of vertical wires spaced from each other and attached to a plurality of horizontal support rings, and the cylindrical tube is attached to the horizontal support rings.

The collector assembly of the invention may have a configuration in which the cylindrical tube is disposed in the internal space delimited by the screen and is concentric with respect to said screen.

Alternatively, the collector assembly of the invention is configured in a manner such that the screen is disposed in the internal space delimited by the cylindrical tube and is concentric with respect to the cylindrical tube.

In a further aspect, the invention concerns a reactor with a radial movement of gaseous fluid, comprising:
   an outer envelope defining a vessel extending along a principal vertical axis and containing a reaction zone comprising a bed of particles of catalyst;
   at least one inlet means for a feed;
   at least one outlet means for effluent produced by the catalytic reaction;
   at least one inlet means for catalyst in order to introduce the catalyst into the reaction zone;
   at least one outlet means for catalyst, opening into the reaction zone; and
   a collector assembly in accordance with the invention, in communication with the effluent outlet means and in which the screen of the collector assembly is in contact with the particles of catalyst of the catalytic bed.

In accordance with one embodiment, the reactor further comprises a cylindrical screen for the distribution of gaseous fluid which is impermeable to catalyst, disposed between the outer envelope and the collector assembly in a manner such as to define an annular distribution zone comprised between the envelope and the cylindrical gaseous fluid distribution screen, an annular catalytic zone comprised between the cylindrical gaseous fluid distribution screen and the collector assembly, and a collector space delimited by the collector assembly.

Alternatively, a reactor in accordance with the invention does not comprise a gaseous fluid distribution screen, but comprises a plurality of gaseous fluid distribution tubes connected to a distribution box and immersing into the annular catalytic zone which is delimited by the vessel and the collector assembly.

In accordance with an alternative embodiment, the reactor further comprises a cylindrical gaseous fluid distribution screen which is impermeable to catalyst and the collector assembly is disposed between the envelope and the cylindrical gaseous fluid distribution screen in a manner such as to define an outer annular collector zone comprised between the envelope and the collector assembly, an annular catalytic zone comprised between the cylindrical gaseous fluid distribution screen and the collector assembly and a distribution space delimited by the cylindrical gaseous fluid distribution screen.

Finally, the invention also concerns a process for the catalytic conversion of a hydrocarbon feed using a reactor in accordance with the invention, in which:
   the hydrocarbon feed in the gaseous form is continuously supplied to a catalytic bed contained in the reactor;
   the hydrocarbon feed passing radially through the catalytic bed is brought into contact with the catalyst in a manner such as to produce a gaseous effluent; and
   said effluent is withdrawn after it has passed through the collector assembly.

The catalytic bed employed is a moving bed, so that the catalyst is sent to the reaction zone continuously or discontinuously and is withdrawn from the reaction zone continuously or discontinuously.

BRIEF DESCRIPTION OF FIGURES

Other characteristics and advantages of the invention will become apparent from the following description which is given purely by way of illustration and is not limiting, accompanied by.

Figure 1:
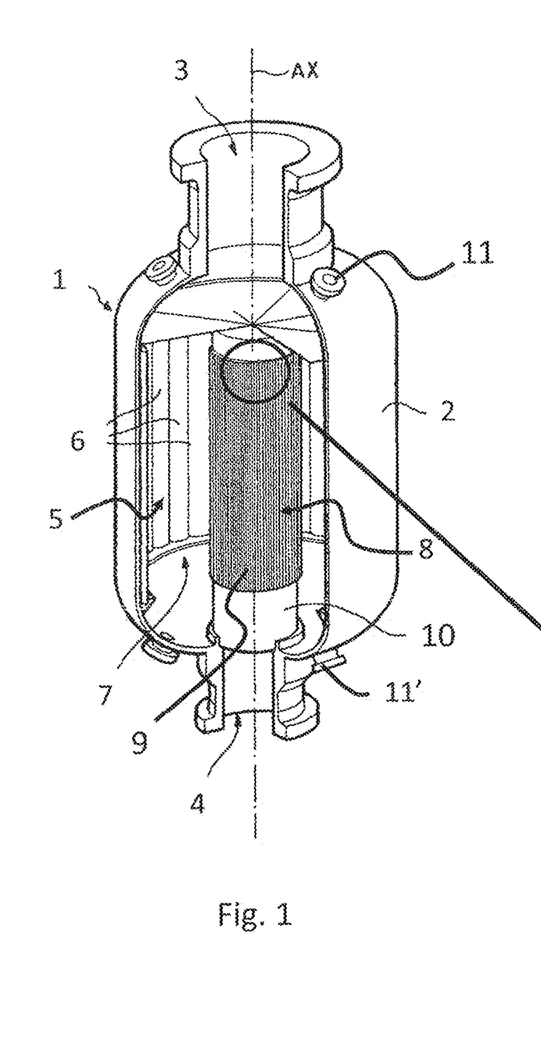
FIG. 1, which shows a perspective view with a partial sectional view of a radial flow reactor in accordance with the prior art.

Referring to FIG. 1, a radial flow reactor 1 in accordance with the prior art has the external appearance of a carboy, forming a cylindrical vessel 2 extending in a vertical axis of symmetry AX. The upper portion of the vessel 2 comprises a first orifice 3 and its lower portion comprises a second orifice 4. The orifices 3 and 4 are respectively intended to be the inlet and outlet for a fluid passing through the reactor 1. It should be noted that the respective functions of the orifices 3 and 4 may be reversed, i.e. the orifice 4 may act as the fluid inlet and the orifice 3 may act as an outlet orifice for reaction effluent.

Inside this cylindrical reservoir is arranged a catalytic bed 7 in the shape of a vertical cylindrical ring defined on the inside by a central collector assembly 8 retaining the catalyst and on the outside by an "external" screen 5 either of the same type as the screen of the collector assembly 8, or by a device consisting of an assembly of screen elements in the form of longitudinally extending shells 6, as can be seen in FIG. 1. These screen elements in the form of shells 6 forming the conduits are also known as "scallops". These conduits 6 are maintained by the reservoir and are close-coupled with the internal face of the vessel, parallel to the axis AX, in order to form a substantially cylindrical internal envelope. The screen elements in the form of scallops 6 are in direct communication with the first orifice 3, for example via their upper end, in order to receive a gaseous stream of feed. The gaseous stream diffuses through the wall of the conduits 6, which is perforated, in order to pass through the bed of solid particles of catalyst 7, converging radially towards the centre of the reactor 1. The feed is then brought into contact with the catalyst in order to undergo chemical transformations, for example a catalytic reforming reaction, and to produce a reaction effluent. The reaction effluent is then collected by the central collector assembly 8 which here is in communication with the second orifice 4 of the reactor. The collector assembly comprises a cylindrical screen 9 and a cylindrical tube 10 disposed in the space circumscribed by the cylindrical screen 9. The screen 9, which acts as a sieve, is designed so as to be permeable to a gaseous fluid and impermeable to particles of catalyst. The cylindrical tube 10 is also perforated, and thus comprises through holes.

In operation, the gaseous fluid introduced into the first orifice 3 is distributed over the height of the reactor and then radially traverses the "external" screen 5, then radially traverses the bed of catalyst particles 7 where it is brought into contact with the catalyst in order to produce an effluent which is subsequently collected by the assembly 8 and evacuated via the second orifice 4.

A reactor of this type may also be operated with a continuous gravitational flow of catalyst in the annular catalytic bed 7. In the case of FIG. 1, the reactor 1 further comprises means 11 for introducing catalyst into the annular bed, disposed in an upper portion of the reactor, and means 11' for withdrawing catalyst which are disposed in a lower portion of the reactor.

The tube 10 is generally attached to the screen 9, for example by being bolted, or by welding or using any other technique which is known to the skilled person.

Figure 2:
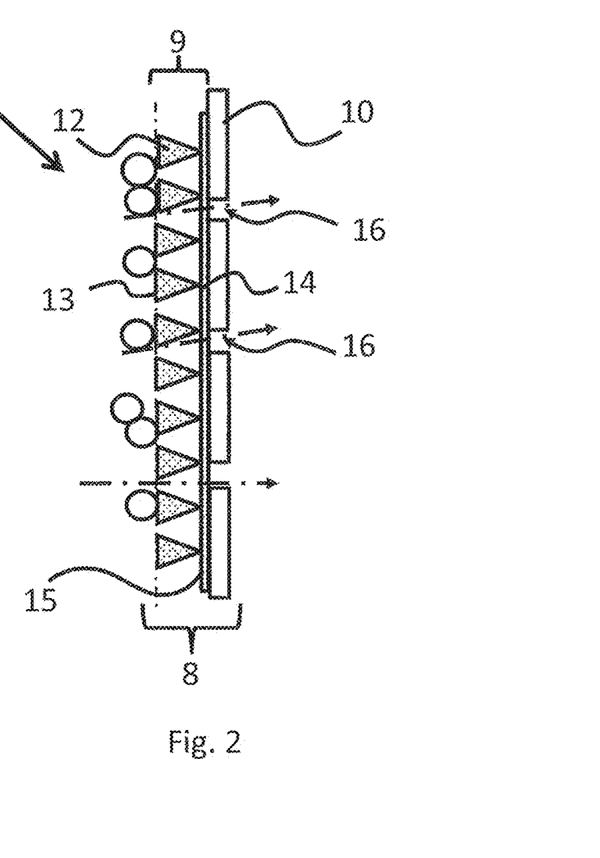
FIG. 2, which is a detailed sectional view in a plane perpendicular to the vertical axis, of a collector assembly in accordance with FIG. 1.

FIG. 2 is a detailed sectional view along a plane perpendicular to the vertical axis AX of a collector assembly 8 in accordance with the invention. The screen 9 is constituted by an assembly of profiled metallic wires 12 disposed parallel to each other along the vertical axis of the collector assembly. As an example, the profile of the wires may be V-shaped.

As indicated in FIG. 2, the vertical wires 12 have a first face 13 and an opposed second face 14. In the context of the invention, the first face 13 corresponds to the face which is in contact with the particles of catalyst of the catalytic bed when the conduit is used in a radial reactor. The second face 14, which may be designated as the "back", corresponds to the face which is not in contact with the bed of catalyst when the conduit is used in a radial reactor. The profiled wires 12 are kept attached together via a series of horizontal metal support rings 15 welded to the second face 14 of the vertical wires at all points of contact with them. The support rings 15 are preferably disposed along the height of the screen 9 in a regular manner. Because of this arrangement of vertical wires 12 and support rings 15, the screen 9 has a wall which is perforated over its periphery. The disposition of the wires 12 and the rings 15 is such that the openings formed are capable of allowing a gaseous fluid to diffuse through while retaining the particles of catalyst.

The collector assembly 8 also comprises a cylindrical tube 10 disposed, for example, in the internal space delimited by the screen 9, which is close-coupled with said screen 9. More precisely, the tube 10 is attached to the "back" side of the profiled wires 12 via the support rings 15. The tube 10 is also provided with a plurality of through holes 16 in a manner such that the gaseous fluid which has diffused radially through the screen can also pass through the tube 10.

It should be noted that in accordance with the invention, the section of the screen and the tube may be in the shape of a polygon with at least 3 sides, it being understood that the number of sides of the sections of the screen and tube are thus equal.

Figure 3:
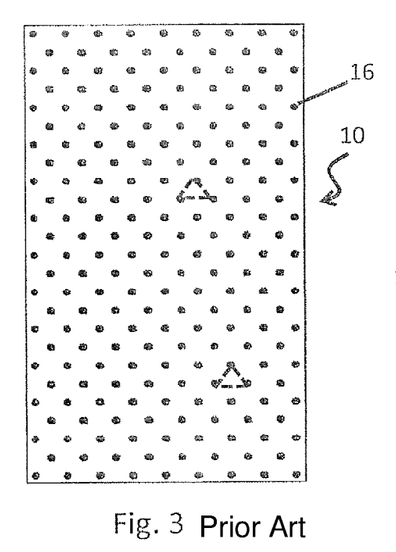
FIG. 3, which is a plan view of a tube of a collector assembly in accordance with the prior art.

We shall refer now to FIG. 3, which is a developed plan view of a tube 10 in accordance with the prior art. The tube 10 may be produced from a perforated metal plate. Typically, a tube in accordance with the prior art comprises a single zone which is permeable to gaseous fluid, comprising through holes 16 which are disposed in a uniform manner over its surface and over the height of said tube. In the example of FIG. 3, the holes 16 are arranged to form a triangular pattern with a regular pitch between adjacent holes.

Figure 4:
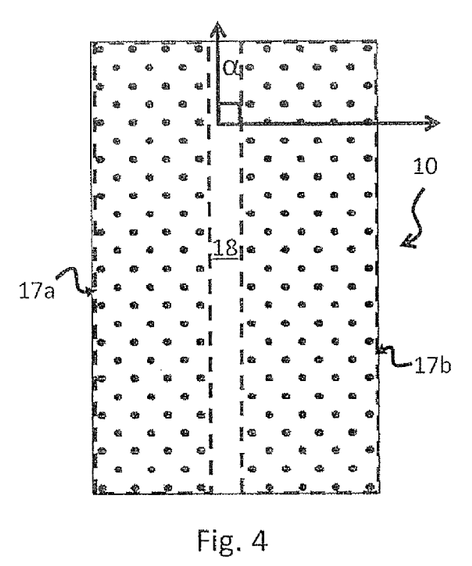
FIGS. 4 to 8, which are plan views of different configurations of a tube in accordance with the invention.

FIG. 4 shows a first embodiment of a tube 10 forming part of the collector assembly of the invention. The tube 10 is composed of a plurality of zones 17a and 17b (see the dashed lines) provided with through holes 16 which are thus permeable to gaseous fluid, and a plurality of zones 18 which are said to have "reduced permeability" to gaseous fluid. As can be seen in FIG. 4, the zones which are permeable to gaseous fluid 17a and 17b have the same configuration as that of the tube of FIG. 3, namely a triangular pattern of through holes 16 with a regular pitch between the adjacent holes. Clearly, it is possible to arrange the through holes 16 in a regular square pattern or rectangular pattern. Alternatively, the through holes may be disposed in a randomized manner. In the context of the invention, a zone with reduced permeability corresponds to a zone with a porosity, defined as the ratio between the total permeable surface area of said zone (i.e. the total surface area of the holes) and the total developed surface area of said zone, which is in the range 0 to 0.005. A zone said to have "reduced permeability" necessarily has a lower porosity than that of a zone said to be "permeable". A zone which is said to be "permeable" thus has a porosity, which is the ratio between the total permeable surface area of said zone (i.e. the total surface area of the holes) and the total developed surface area of said zone, of more than 0.0055 and preferably in the range 0.0055 to 0.08, and more preferably in the range 0.0065 to 0.065.

By way of example, if a zone with a reduced permeability has a total developed surface area of 1 m² and comprises 50 through holes with a 1.12 cm radius, the porosity of said zone is equal to:

$$P=(50\times(\pi\times(1.12\times10^{-2})^2))/(1)=0.02$$

In the embodiment of FIG. 4, the zone with reduced permeability has a porosity of 0 and corresponds to a solid, impermeable zone which has no through holes, it being understood that an impermeable solid zone excludes any solid space comprised between the through holes of a permeable zone.

In accordance with the invention, a zone with "reduced permeability" may extend at an angle α with respect to the horizontal which is in the range 0° to 90°. In the example of FIG. 4, the zone with "reduced permeability" 18 is a solid zone forming a continuous solid strip extending along the vertical axis of the tube, i.e. forming an angle α with respect to the horizontal equal to 90°.

In accordance with the invention, a tube may comprise a plurality of zones which are permeable to gaseous fluid which are separated by a zone with "reduced permeability" to gaseous fluid.

Figure 5:
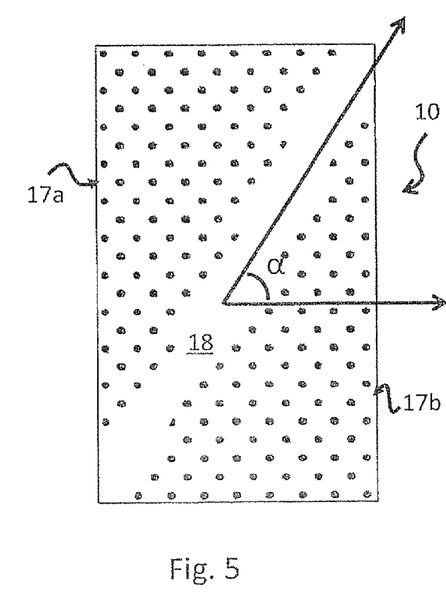

FIG. 5 represents another configurational form of the tube 10 of the collector assembly of the invention, which is distinguished from that of FIG. 4 in that the zone with "reduced permeability" 18 (in this case a solid continuous zone) extends in a direction which forms an angle α with respect to the horizontal substantially equal to 45°. When the tube is rolled up, the zone with "reduced permeability" 18 forms a helix or a portion of a helix around the tube.

In the context of the invention, the tube of the collector assembly may comprise a single zone with "reduced permeability" forming a continuous helix around the tube or, alternatively, a plurality of helices or a plurality of helical portions parallel to each other around the tube.

Figure 6:
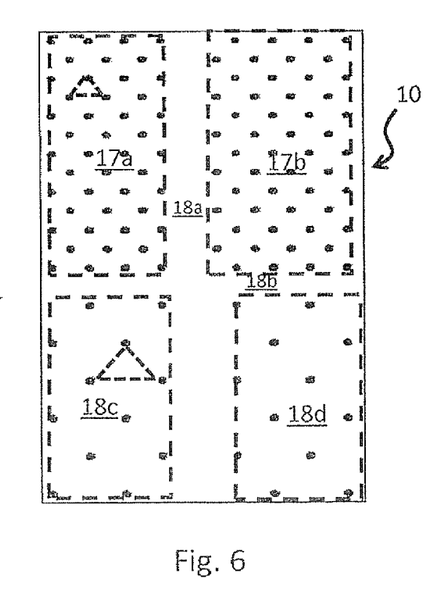

FIG. 6 shows another embodiment in which the tube comprises a plurality of zones permeable to gaseous fluid, in this case two permeable zones 17a, 17b and four zones with "reduced permeability" 18a, 18b, 18c and 18d. The solid zones 18a and 18b cross over and respectively extend in a direction forming an angle α with respect to the horizontal of 90° and 0° respectively. The tube further comprises two other zones with "reduced permeability" 18c and 18d in the lower portion of the tube, which are separated from each other by the solid zone 18a and the permeable zones 17a and 17b via the solid zone 18b respectively. The porosity of the zones 18c and 18d is reduced with respect to that of the zones 17a and 17b (said to be permeable) by increasing the pitch between the through holes (and thus by reducing the density of the through holes) in the zones.

This embodiment illustrates the fact that it is possible to vary the pressure drop locally as a function of the height of the tube of the collector assembly in order to maintain a constant flow of gas along the collector assembly, and thus in the catalytic bed, and thus to limit the formation of preferential pathways (channelling) in the catalytic bed.

The reduction in the permeability of a zone generates an increase in the pressure drop at that zone. In the case where the gaseous fluid moves in a radial ascending movement, this is subjected to a larger pressure drop at the head of the reactor. In order to ensure a uniform flow of gas over the height of the screen of the collector, it is thus advantageous to generate a pressure drop in the lower section of the screen by means of a cylindrical tube which then includes zones with reduced permeability in its lower section, while its upper section may be free of a zone with reduced permeability.

The arrangement of permeable zones and zones with reduced permeability is reversed when the collector assembly is used in a reactor in which the gaseous fluid is injected into the head of said reactor and the reaction effluent is recovered from the bottom of the reactor. In such a situation, the pressure drop is higher at the bottom of the reactor than at the head of the reactor.

Another advantage of using a collector assembly in accordance with the invention in a moving catalyst bed reactor described with reference to FIG. 1 is that it can reduce the size of a reactor of this type. In fact, the space for distributing gaseous fluid comprised between the reactor and the distribution screen can be reduced, even at the price of increasing the pressure drop to which the fluid is subjected in this space which may be taken up at the level of the collector assembly of the invention by adapting the porosity at the level of the cylindrical tube.

Figure 7:
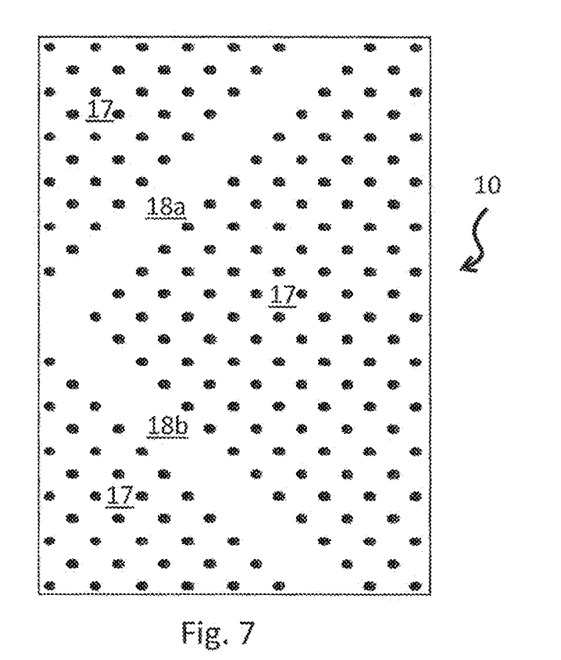

FIG. 7 represents another configurational mode of a tube 10 of the collector assembly in accordance with the invention, in which the zones 18a and 18b with "reduced permeability" compared with the permeable zones 17, which here are solid zones, respectively extend to form an angle α and −α with respect to the horizontal and meet at one of their ends in a manner such as to form a solid continuous strip with a "V" shape. As an alternative to this embodiment, two zones 18a and 18b with "reduced permeability" may cross each other in the shape of an X with a first "reduced permeability" zone inclined at an angle α with respect to the horizontal and a second zone with "reduced permeability" inclined at an angle −α with respect to the horizontal. These embodiments may be refined in a manner such that the tube is lined with a plurality of "reduced permeability" zones with a "V" and/or "X" shape around said tube.

Figure 8:
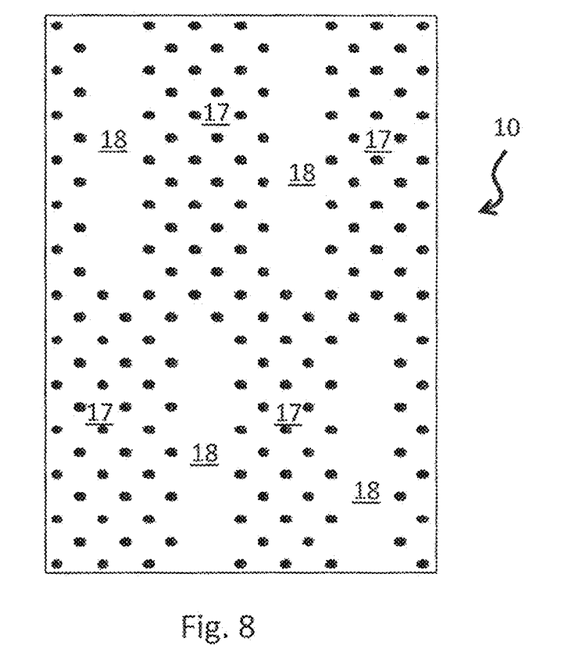

Another embodiment of the tube of the collector assembly of the invention is represented in plan in FIG. 8. The tube comprises a plurality of zones which are permeable to gaseous fluid and a plurality of zones 18 said to be of "reduced permeability" to gaseous fluid which are disposed in a manner such that a portion of the "reduced permeability" zones are located in the upper half of the tube and another portion of the zones with "reduced permeability" are located in the lower half of the tube. In the embodiment of FIG. 8, the zones with "reduced permeability" 18 are also arranged alternately in the upper half and in the lower half of the tube.

Irrespective of the disposition of the zones with "reduced permeability", these preferably extend over a distance in the range 10% to 100% of the height of the tube, and more preferably in the range 50% to 100% of the height of the tube.

The number of zones with "reduced permeability" to gaseous fluid and their dimensions may be selected in a manner such that the total developed surface area of said zones with "reduced permeability" is in the range 1% to 30% of the total developed surface area of the tube.

It should also be noted that in the context of the invention, it is possible to use the size of the surface area of the through holes and/or the number of holes as factors for modifying the porosity of the zones with "reduced permeability". In accordance with the invention, the through holes may have any sectional shape, for example circular, triangular, square or indeed rectangular.

Surprisingly, the Applicant has established that, for the same velocity of gas passing through the collector assembly (screen+perforated tube), using a tube comprising zones with "reduced permeability" to gaseous fluid means that the thickness of the cake of particles pinned by the stream of gas, compared with a prior art collector assembly constituted by a screen to which a tube not comprising such zones with "reduced permeability" is close-coupled, is limited. The presence of these zones with "reduced permeability" thus means that zones can be generated on the screen where the particles are pinned to a lesser extent and on which the cake of solid cannot develop, with the effect of limiting the thickness of the cake formed on the screen. Thus, by reducing the quantity of catalyst "pinned" by the cake, the proportion of "inactive" catalyst is reduced, and thus the catalytic performance of the reactor is improved.

The invention also pertains to a process for the catalytic treatment of a hydrocarbon feed in a radial reactor with a moving bed of catalyst. The reactor in accordance with the invention comprises:

- an envelope defining a vessel extending along a principal vertical axis and containing a reaction zone comprising a bed of particles of catalyst;
- at least one inlet means for a feed;
- at least one outlet means for effluent produced by the catalytic reaction;
- at least one inlet means for catalyst in order to introduce the catalyst into the reaction zone;
- at least one outlet means for catalyst, opening into the reaction zone; and
- a collector assembly in accordance with the invention for effluent disposed in the reaction zone and in communication with the effluent outlet means.

Furthermore, the reactor may optionally include a screen which is said to be "for distributing gaseous fluid" which is permeable to gas and impermeable to particles of catalyst, which is disposed in the vessel in a concentric manner with respect to the collector assembly and the screen of the collector assembly being in contact with the particles of catalyst of the catalytic bed.

Figure 9:
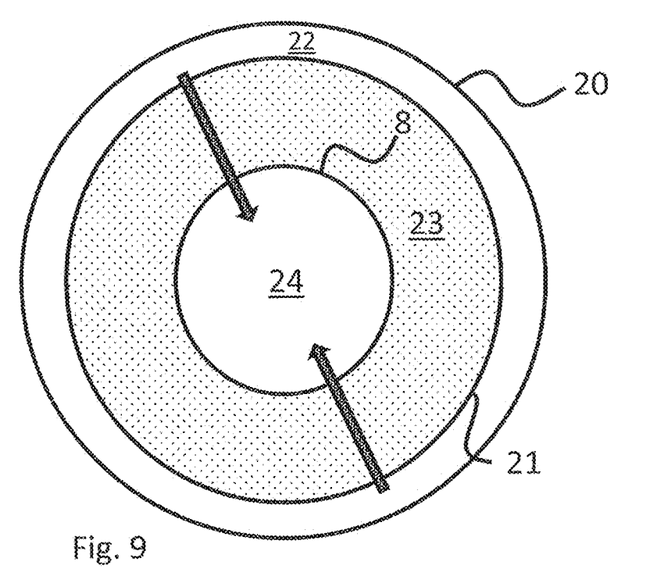
FIG. 9, which is a sectional view of a reactor in accordance with the invention, in a plane perpendicular with respect to the vertical axis of the reactor.

One embodiment of the reactor in accordance with the invention, represented in FIG. 9, is a centripetal radial movement reactor (i.e. the gas stream moves from the periphery of the vessel towards the centre of the vessel). The reactor comprises an envelope 20 which delimits a vessel in which a cylindrical screen termed the "external" screen 21 which is permeable to gas and impermeable to catalyst and a collector assembly 8 in accordance with the invention are disposed. The external screen 21 is disposed between the envelope 20 and the collector assembly 8 in a concentric manner with respect to the collector assembly. The collector assembly 8 is disposed in a manner such that the collector screen (not shown) is in contact with the catalyst. In a configuration of this type, the reactor comprises an "external" annular zone 22 comprised between the envelope 20 and the "external" screen 21, an annular catalytic zone 23 comprised between the "external" screen 21 and the collector assembly 8 and a cylindrical collector space 24 delimited by the collector assembly 8. The "external" screen 21 may take the form of a perforated plate or a screen formed by a network of wires and profiled metal rods, or indeed an assembly of screen elements in the form of a shell (or "scallop"). In operation, the gaseous feed is injected into the annular distribution zone 22 either via the bottom or via the top of the reactor, then passes through the screen 21 denoted as the "external" screen, and then passes in a substantially radial manner through the bed of particles of catalyst in the annular catalytic zone 23. In the annular catalytic zone 23, the gaseous fluid is brought into contact with the catalyst in order to produce a gaseous reaction effluent which is collected in the space 24 of the collector assembly 8 and which is then withdrawn either from the top of the reactor (when the feed has been introduced into the bottom of the reactor) or from the bottom of the reactor (when the feed has been introduced via the top of the reactor).

In an alternative embodiment (not shown), the reactor does not include a cylindrical screen 21, but a plurality of distribution tubes connected to a distribution box (inside or outside the reactor) and immersing into the reaction zone, which can then be used to distribute the gaseous feed in the catalytic zone 23.

Figure 10:
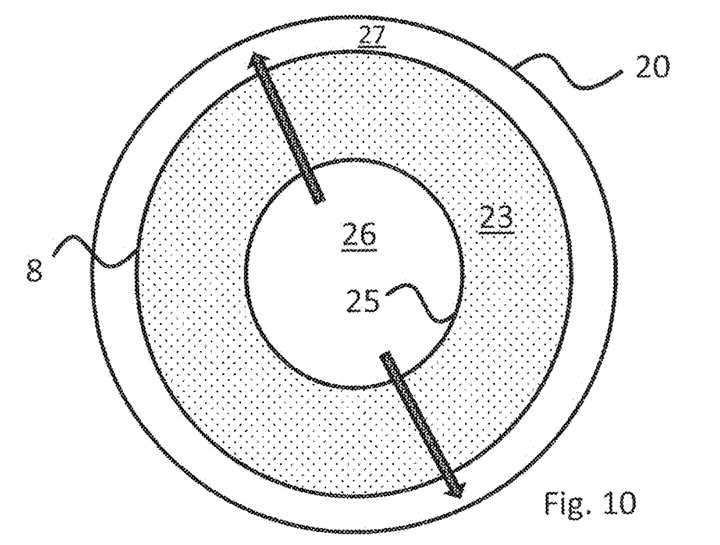
FIG. 10, which is a sectional view of a reactor in accordance with another embodiment, in a perpendicular plane with respect to the vertical axis of the reactor.

A further embodiment of the reactor of the invention is shown in FIG. 10, which uses a collector assembly 8 in accordance with the invention disposed between the vessel 20 and a cylindrical distribution screen 25 for gaseous fluid which is arranged in the centre of the vessel 20. The screen 25 may be of the same type as the screen 21 described with reference to FIG. 9. It should be noted that in this configuration, the collector assembly is disposed in the reactor in a manner such that the collector screen (not shown in FIG. 10) is in direct contact with the catalyst.

As can be seen in FIG. 10, the reactor comprises a cylindrical zone 26 in which the gaseous fluid moves, an annular catalytic zone 23 delimited by the distribution screen 25 and the collector assembly 8 and an outer cylindrical collector zone 27 defined between the vessel 20 and the collector assembly 8. This configuration of the reactor is adapted to treat a gaseous fluid which moves in a radial manner in a centrifugal direction, as represented by the arrows in FIG. 10. The gaseous feed is injected into the cylindrical distribution zone 26 either via the bottom or via the top of the reactor, then passes through the screen 25 and then passes in a substantially radial manner through the bed of particles of catalyst of the annular catalytic zone 23. In the annular catalytic zone 23, the gaseous fluid is brought into contact with the catalyst in order to produce a gaseous reaction effluent which is collected in the collector space 27 comprised between the vessel and the collector assembly 8. The reaction effluent is then withdrawn either from the top of the reactor (when the feed has been introduced into the bottom of the reactor) or from the bottom of the reactor (when the feed has been introduced via the top of the reactor).

In an embodiment which has not been shown, a reactor in accordance with the invention does not comprise a gaseous fluid distribution screen, but comprises a plurality of gaseous fluid distribution tubes connected to a distribution box and immersing into the annular catalytic zone which is delimited by the vessel and the collector assembly.

The reactor in accordance with the invention may be a reactor with a moving catalytic bed where the catalyst is introduced into the reactor continuously or discontinuously and removed from said reactor continuously or discontinuously.

The reactor and the process of the invention may be applied to reactions with a radial movement of gaseous fluid such as, for example, a reaction for the catalytic reforming of a hydrocarbon cuts, a skeletal olefins isomerization reaction, metathesis for the production of propylene, or an oligocracking reaction.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 15/51.832, filed Mar. 5, 2015, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A collector assembly (8) for a gaseous fluid suitable for being disposed in a reaction section with a moving bed of catalyst of a radial reactor, said collector assembly comprising:
a vertical cylindrical screen (9) which is permeable to gaseous fluid and impermeable to particles of catalyst, and a vertical cylindrical tube (10) which R supported by said screen (9) and disposed in a concentric manner with respect to said screen, said cylindrical tube being permeable to gaseous fluid and impermeable to particles of catalyst,
said cylindrical tube (10) comprising one or more permeable zones (17a, 17b) which are permeable to gaseous fluid comprising a plurality of through holes and a plurality of reduced permeability zones (18a, 18b, 18c, 18d) having reduced permeability to gaseous fluid compared with said one or more permeable zones, each reduced permeability zone having a lower porosity than that of each of said one or more permeable zones, the porosity of each zone being defined as the ratio between the total permeable surface area of said zone and the total developed surface area of said zone, and in which the porosity of each reduced permeability zone is other than 0 and up to 0.005, wherein a reduced permeability zone excludes any space comprised between the through holes of said one or more permeable zones,
wherein the total developed surface area of the reduced permeability zones is in the range 1% to 30% of the total developed surface area of the cylindrical tube, and
wherein each reduced permeability zone comprises through holes.

2. The collector assembly according to claim 1, wherein the screen (9) and the cylindrical tube (10) are polygonal in shape with at least 3 sides, wherein the number of sides of the screen and the number of sides of the cylindrical tube are equal.

3. The collector assembly according to claim 1, wherein the through holes of said reduced permeability zone are spaced from each other by a pitch which is higher than the pitch between the through holes of said one or more permeable zones.

4. The collector assembly according to claim 1, wherein the surface area of the through holes of said reduced permeability zone is smaller than the surface area of the through holes of said one or more permeable zones.

5. The collector assembly according to claim 1, wherein the reduced permeability zones are extended, forming an angle α in the range 0° to 90° with respect to the horizontal.

6. The collector assembly according to claim 1, wherein the screen (9) is formed by a plurality of vertical wires (12) spaced from each other and attached to a plurality of horizontal support rings (15), and the cylindrical tube (10) is attached to the horizontal support rings (15).

7. The collector assembly according to claim 1, wherein the cylindrical tube (10) is disposed in an internal space delimited by the screen (9).

8. The collector assembly according to claim 1, wherein the screen (9) is disposed in an internal space delimited by the cylindrical tube (10).

9. The collector assembly according to claim 1, wherein said one or more permeable zones have a porosity of more than 0.0055.

10. The collector assembly according to claim 1, wherein said one or more permeable zones have a porosity in the range 0.0055 to 0.08.

11. The collector assembly according to claim 1, wherein said one or more permeable zones have a porosity in the range 0.0065 to 0.065.

12. The collector assembly according to claim 1, wherein said plurality of reduced permeability zones comprises a first reduced permeability zone that forms an angle α with respect to the horizontal and a second reduced permeability zone that forms an angle −α with respect to the horizontal and said first and second reduced permeability zones meet to form a V shape.

13. The collector assembly according to claim 1, wherein said plurality of reduced permeability zones comprises a first reduced permeability zone that forms an angle α with respect to the horizontal and a second reduced permeability zone that forms an angle −α with respect to the horizontal and said first and second reduced permeability zones cross each other in the shape of an X.

14. The collector assembly according to claim 1, wherein said plurality of reduced permeability zones comprises a first group of reduced permeability zones located in an upper half of the tube and a second group of reduced permeability zones located in a lower half of the tube, wherein the reduced permeability zones of the first group of reduced permeability zones are offset from the reduced permeability zones of the second group of reduced permeability zones.

15. The collector assembly according to claim 1, wherein said plurality of reduced permeability zones extend over a distance in the range 10% to 100% of the height of the cylindrical tube.

16. The collector assembly according to claim 1, wherein said plurality of reduced permeability zones extend over a distance in the range 50% to 100% of the height of the cylindrical tube.

17. The collector assembly according to claim 1, wherein said cylindrical tube having an upper section and a lower section, and wherein said plurality of reduced permeability zones are in said lower section of the cylindrical tube and said upper section of the cylindrical tube is free of said reduced permeability zones.

18. The collector assembly according to claim 1, wherein said cylindrical tube having an upper section and a lower section, and wherein said plurality of reduced permeability zones are in said upper section of the cylindrical tube and said lower section of the cylindrical tube is free of said reduced permeability zones.

19. A radial reactor comprising:
an outer envelope (20) defining a vessel extending along a principal vertical axis and containing a reaction zone comprising a bed of catalyst particles;
at least one inlet means for introducing a feed into said reactor;
at least one outlet means for removing effluent produced by the catalytic reaction from said reactor;
at least one inlet means for introducing catalyst into the reaction zone;
at least one outlet means for removing catalyst, opening into the reaction zone; and
a collector assembly (8) according to claim 1, in communication with the at least one outlet means for removing effluent and wherein the screen of the collector assembly is in contact with the catalyst particles of the bed.

20. The reactor according to claim 19, further comprising a cylindrical screen (21) for distribution of gaseous fluid which is impermeable to said catalyst particles, disposed between the external envelope and the collector assembly in a manner such as to define an annular distribution zone (22) comprised between the envelope (20) and the cylindrical gaseous fluid distribution screen (21), an annular catalytic zone (23) comprised between the cylindrical gaseous fluid distribution screen (21) and the collector assembly (8), and a collector space (24) delimited by the collector assembly (8).

21. The reactor according to claim 19, further comprising a cylindrical gaseous fluid distribution screen (25) which is impermeable to catalyst, and wherein the collector assembly (8) is disposed between the envelope (20) and the cylindrical gaseous fluid distribution screen (25) in a manner such as to define an outer annular collector zone (27) comprised between the envelope (20) and the collector assembly (8), an annular catalytic zone (23) comprised between the cylindrical gaseous fluid distribution screen (25) and the collector assembly (8) and a distribution space (26) delimited by the cylindrical gaseous fluid distribution screen (25).

22. A reactor according to claim 19, wherein said at least one inlet means for introducing catalyst into the reaction zone is in an upper portion of the reactor, and said at least one outlet means for removing catalyst is in a lower portion of the reactor.

23. A method for operating a radial reactor according to claim 22, said method comprising:
continuously supplying gaseous feed to said bed of catalyst particles contained in the reactor;
passing the gaseous feed radially through the bed whereby the gaseous feed is brought into contact with the catalyst in a manner such as to produce a gaseous effluent; and
withdrawing said effluent after said effluent has passed through the collector assembly;
wherein said bed of catalyst particles is a moving bed and said method further comprises introducing catalyst particles to said moving bed, continuously or discontinuously, via said at least one inlet means for introducing catalyst into the reaction zone, and withdrawing catalyst particles from said moving bed, continuously or discontinuously, via said at least one outlet means for removing catalyst from the reaction zone.

24. A process for the catalytic conversion of a hydrocarbon feed using a reactor in accordance with claim 19, said process comprising:
continuously supplying the hydrocarbon feed in the gaseous form to said bed of catalyst particles contained in the reactor;
passing the hydrocarbon feed radially through the bed whereby the feed is brought into contact with the catalyst in a manner such as to produce a gaseous effluent; and
withdrawing said effluent after said effluent has passed through the collector assembly.

25. The process according to claim 24, wherein the bed of catalyst particles is a moving bed and the catalyst is introduced into the reactor continuously or discontinuously and respectively withdrawn from said reactor continuously or discontinuously.

26. A collector assembly (8) for a gaseous fluid suitable for being disposed in a reaction section with a moving bed of catalyst of a radial reactor, said collector assembly comprising:
a vertical cylindrical screen (9) which is permeable to gaseous fluid and impermeable to particles of catalyst, and a vertical cylindrical tube (10) which is supported by said screen (9) and disposed in a concentric manner with respect to said screen, said cylindrical tube being permeable to gaseous fluid and impermeable to particles of catalyst,
said cylindrical tube (10) comprising one or more permeable zones (17a, 17b) which are permeable to gaseous fluid comprising a plurality of through holes and a plurality of reduced permeability zones (18a, 18b, 18c, 18d) having reduced permeability to gaseous fluid compared with said one or more permeable zones, each reduced permeability zone having a lower porosity than that of each of said one or more permeable zones, the porosity of each zone being defined as the ratio between the total permeable surface area of said zone and the total developed surface area of said zone, and in which the porosity of each reduced permeability zone is in the range 0 to 0.005, wherein a reduced permeability zone excludes any space comprised between the through holes of said one or more permeable zones,
wherein the total developed surface area of the reduced permeability zones is in the range 1% to 30% of the total developed surface area of the cylindrical tube,
wherein said plurality of reduced permeability zones extend over a distance in the range 50% to 100% of the height of the cylindrical tube.

27. A collector assembly (8) for a gaseous fluid suitable for being disposed in a reaction section with a moving bed of catalyst of a radial reactor, said collector assembly comprising:
a vertical cylindrical screen (9) which is permeable to gaseous fluid and impermeable to particles of catalyst, and a vertical cylindrical tube (10) which is supported by said screen (9) and disposed in a concentric manner with respect to said screen, said cylindrical tube being permeable to gaseous fluid and impermeable to particles of catalyst,
said cylindrical tube (10) comprising one or more permeable zones (17a, 17b) which are permeable to gaseous fluid comprising a plurality of through holes and a plurality of reduced permeability zones (18a, 18b, 18c, 18d) having reduced permeability to gaseous fluid compared with said one or more permeable zones, each reduced permeability zone having a lower porosity than that of each of said one or more permeable zones, the porosity of each zone being defined as the ratio between the total permeable surface area of said zone and the total developed surface area of said zone, and in which the porosity of each reduced permeability zone is in the range 0 to 0.005, wherein a reduced permeability zone excludes any space comprised between the through holes of said one or more permeable zones, wherein the total developed surface area of the reduced permeability zones is in the range 1% to 30% of the total developed surface area of the cylindrical tube, wherein said plurality of reduced permeability zones comprises a first reduced permeability zone that forms an angle $\alpha$ with respect to the horizontal and a second reduced permeability zone that forms an angle $-\alpha$ with respect to the horizontal and said first and second reduced permeability zones meet to form a V shape.

28. A collector assembly (8) for a gaseous fluid suitable for being disposed in a reaction section with a moving bed of catalyst of a radial reactor, said collector assembly comprising:

a vertical cylindrical screen (9) which is permeable to gaseous fluid and impermeable to particles of catalyst, and a vertical cylindrical tube (10) which is supported by said screen (9) and disposed in a concentric manner with respect to said screen, said cylindrical tube being permeable to gaseous fluid and impermeable to particles of catalyst, said cylindrical tube (10) comprising one or more permeable zones (17a, 17b) which are permeable to gaseous fluid comprising a plurality of through holes and a plurality of reduced permeability zones (18a, 18b, 18c, 18d) having reduced permeability to gaseous fluid compared with said one or more permeable zones, each reduced permeability zone having a lower porosity than that of each of said one or more permeable zones, the porosity of each zone being defined as the ratio between the total permeable surface area of said zone and the total developed surface area of said zone, and in which the porosity of each reduced permeability zone is in the range 0 to 0.005, wherein a reduced permeability zone excludes any space comprised between the through holes of said one or more permeable zones, wherein the total developed surface area of the reduced permeability zones is in the range 1% to 30% of the total developed surface area of the cylindrical tube, wherein said plurality of reduced permeability zones comprises a first reduced permeability zone that forms an angle $\alpha$ with respect to the horizontal and a second reduced permeability zone that forms an angle $-\alpha$ with respect to the horizontal and said first and second reduced permeability zones cross each other in the shape of an X.

29. A collector assembly (8) for a gaseous fluid suitable for being disposed in a reaction section with a moving bed of catalyst of a radial reactor, said collector assembly comprising:

a vertical cylindrical screen (9) which is permeable to gaseous fluid and impermeable to particles of catalyst, and a vertical cylindrical tube (10) which is supported by said screen (9) and disposed in a concentric manner with respect to said screen, said cylindrical tube being permeable to gaseous fluid and impermeable to particles of catalyst, said cylindrical tube (10) comprising one or more permeable zones (17a, 17b) which are permeable to gaseous fluid comprising a plurality of through holes and a plurality of reduced permeability zones (18a, 18b, 18c, 18d) having reduced permeability to gaseous fluid compared with said one or more permeable zones, each reduced permeability zone having a lower porosity than that of each of said one or more permeable zones, the porosity of each zone being defined as the ratio between the total permeable surface area of said zone and the total developed surface area of said zone, and in which the porosity of each reduced permeability zone is in the range 0 to 0.005, wherein a reduced permeability zone excludes any space comprised between the through holes of said one or more permeable zones, wherein the total developed surface area of the reduced permeability zones is in the range 1% to 30% of the total developed surface area of the cylindrical tube, wherein said plurality of reduced permeability zones comprises a first group of reduced permeability zones located in an upper half of the tube and a second group of reduced permeability zones located in a lower half of the tube, wherein the reduced permeability zones of the first group of reduced permeability zones are offset from the reduced permeability zones of the second group of reduced permeability zones.

\* \* \* \* \*